(12) United States Patent
Wei et al.

(10) Patent No.: US 7,285,534 B2
(45) Date of Patent: Oct. 23, 2007

(54) CORTICOTROPIN-RELEASING HORMONE ANALOGS AND THEIR USES

(75) Inventors: Edward Wei, Berkeley, CA (US); Kurt Carlson, Sausalito, CA (US)

(73) Assignee: The Regents of the University of California, Oakland, CA (US)

( * ) Notice: Subject to any disclaimer, the term of this patent is extended or adjusted under 35 U.S.C. 154(b) by 233 days.

(21) Appl. No.: 11/006,296

(22) Filed: Dec. 6, 2004

(65) Prior Publication Data

US 2005/0096275 A1    May 5, 2005

Related U.S. Application Data

(62) Division of application No. 10/106,588, filed on Mar. 25, 2002, now Pat. No. 6,849,600.

(51) Int. Cl.
  A61K 38/12 (2006.01)
  A61K 38/17 (2006.01)
  C07K 14/47 (2006.01)
(52) U.S. Cl. ............. 514/12; 514/2; 514/9; 530/300; 530/317; 530/324; 930/21; 930/270
(58) Field of Classification Search ............ None
  See application file for complete search history.

(56) References Cited

U.S. PATENT DOCUMENTS

| | | | |
|---|---|---|---|
| 4,677,191 A | 6/1987 | Tanaka et al. | |
| 4,728,721 A | 3/1988 | Yamamoto et al. | |
| 4,801,612 A | 1/1989 | Wei et al. | |
| 5,116,868 A | 5/1992 | Chen et al. | |
| 5,137,871 A | 8/1992 | Wei | |
| 5,480,869 A | 1/1996 | Wei et al. | |
| 5,777,073 A | 7/1998 | Rivier | |
| 5,824,771 A | 10/1998 | Rivier | |
| 5,844,074 A | 12/1998 | Rivier | |
| 5,869,450 A | 2/1999 | Wei et al. | |
| 6,319,900 B1 | 11/2001 | Wei et al. | |
| 6,849,600 B2 | 2/2005 | Wei et al. | |

OTHER PUBLICATIONS

Slominski et al. Corticotropin releasing hormone and the skin. Frontiers in Biosci. 11: 2230-2248, Sep. 1, 2006.*
Beyermann et al. A Single-Point Slight Alteration Set as a Tool for STructure-Activity Relationship Studies of Ovine Corticotropin Releasing Factor. J. Med. Chem. 39:3324-3330, 1996.
Carlson, et al., "Inhibition of Mouse Melanoma Cell Proliferation by Corticotropin-Releasing Hormone and its Analogs," AntiCancer Research, 21: 1173-1180 (2001).
Dautzenberg and Hauger, "The CRF peptide family and their receptors: yet more partners discovered," Trends in Pharm. Sci., vol. 23, 2002, pp. 71-77.
Gulyas et al. Potent, structurally constrained agonists and competitive antagonists of corticotropin-releasing factor. Proc. Natl. Acad. Sci. USA 92: 10575-10579, Nov. 1995.
Koerber et al., "Constrained Corticotropin-Releasing Factor (CRF) Agonists and Antagonists with i-(i+3) Glu-Xaa-pXbb-Lys Bridges," J. Med. Chem., vol. 41, 1998, pp. 5002-5011.
Komreich et al., "Alanine Series of ovine Corticotropin Releasing Factor (oCRF): A Structure-Activity Relationshiop Study," J. Med. Chem., vol. 35, 1992, pp. 1870-1876.
Rivier et al. Single Point D-Substituted Corticotropin-Releasing Factor Analogues: Effects on Potency and Physicochemical characteristics. J. Med. Chem. 36: 2851-2859, 1993.
Slominski et al., "Characterization of corticotropin-releasing hormone (CRH) in human skin," J. Clin. Endocrin. Metab., vol. 83, 1998, pp. 1020-1024.
Slominski et al., "Expression of proopiomelanocortin (POMC)-derived melanocyte-stimulating hormone (MSH) and adrenocorticotropic hormone (ACTH) peptides in skin of basal cell carcinoma patients" Hum. Pathol., vol. 30, 1999, pp. 208-215.
Slominski et al., "Proopiomelanocortin, corticotropin releasing hormone and corticotropin releasing hormone receptor genes are expressed in human skin," FEBS Letters, vol. 374, 1999, pp. 113-116.
Stein, J.H., editor, Internal Medicine, Chapter 216, "Psoriasis," 1998, pp. 1300-1302.
Theohardies et al., "Corticotropin-releasing hormone induces skin mast cell degranulation and increased vascular permeability, a possible explaination for its proinflammatory effects," Endocrinology, vol. 139, 1998, pp. 403-413.
Tjuvajev et al., "Anti-Neoplastic Properties of Human Corticotropin releasing Factor: Involvement of the Nitric Oxide Pathway," In Vivo, vol. 12, 1998, pp. 1-10.
Wei and Thomas, "Correlation of Neuroendocrine and Anti-Edema Activites of Alanine-Corticotropin-Releasing Factor Analogs," European Journal of Pharmacology, vol. 263, 1994, pp. 319-321.
Wei et al., "D-Amino Acid-Substituted Analogs of Corticotropin-Releasing Hormone (CRH) and Urocortin with Selective Agonist Activity at CRH.sub.1 and CRH.sub.2.beta. Receptors," Peptides, vol. 19, 1998, pp. 1183-1190.

* cited by examiner

*Primary Examiner*—Christine J. Saoud
(74) *Attorney, Agent, or Firm*—Townsend & Townsend and Crew LLP

(57) ABSTRACT

This invention provides members of the corticiotropin-releasing hormone superfamily and peptide analogs thereof wherein the 38th amino acid from the N-terminus is D-Nle, i.e. [D-Nle[38]]-CRH peptide. The peptide analogs can be used to treat proliferative disorders of the skin such as melanoma.

3 Claims, No Drawings

CORTICOTROPIN-RELEASING HORMONE ANALOGS AND THEIR USES

This application is a divisional of application Ser. No. 10/106,588, filed Mar. 25, 2002, now U.S. Pat. No. 6,849,600, the disclosure of which is incorporated herein by reference in its entirety.

FIELD OF THE INVENTION

This invention relates to peptide analogs of corticotropin-releasing hormone and their use for treatment of proliferative disorders of the skin and other tissues.

BACKGROUND OF THE INVENTION

Corticotropin-releasing hormone (CRH, also called CRF or corticoliberin) was first characterized as a 41-residue peptide isolated from ovine hypothalami by Vale et al. (1981). Subsequently, the sequence of human-CRH was deduced from cDNA studies and shown to be identical to that of rat-CRH. Caprine, bovine, porcine, and white sucker fish CRH have also been characterized. The sequences of CRH from hoofed animals are considerably different from the human sequence, but the pig and fish sequences differ from the human/rat sequence by only 2 out of 41 residues.

Peptides with sequences homologous to that of mammalian CRH are found in cells of certain frog skins and in the urophysis of fish. The sequence of sauvagine, a 40-amino acid peptide isolated from the skins of Phyllomedusa frogs, was reported several years before Vale's description of ovine-CRH. The structure of sucker fish urotensin I was reported just months after the description of ovine-CRH and resulted from an independent line of inquiry by Lederis's group in Canada. Although sauvagine and urotensin I are known to induce release of adrenocorticotropin (ACTH) from the pituitary, the primary function of these peptides remains unknown.

In humans, CRH regulates, via release of proopiomelanocortin, ACTH secretion from the anterior pituitary and has several direct actions on central and peripheral tissues. CRH has also been found to have direct anti-inflammatory properties. More recently, evidence has been provided that mammalian skin cells both produce CRH and express functional CRH receptors (Slominski et al., *FEBS Lett.*, 374, pp. 113-116, 1995; Slominski et al., *J. Clin. Endocrinol. Metab.*, 83, pp. 1020-1024, 1998; Slominski et al., *Hum. Pathol.*, 30, pp. 208-215, 1999), although it was not known whether locally produced CRH had an additional role in the physiology of the skin other than as a vasodilator and inhibitor of thermal injury-induced edema.

Some therapeutic methods and uses for CRH are described by Wei et al. in U.S. Pat. No. 4,801,612, issued Jan. 31, 1989, entitled "Method of Inhibiting Inflammatory Response," and U.S. Pat. No. 5,137,871, issued Apr. 26, 1994, entitled "Treatment to Reduce Edema for Brain and Musculature Injury." These patents describe the use of CRH to decrease the leakage of blood components into tissues produced by various adverse medical conditions, and thus to treat a patient for injury to or disease of the brain, central nervous system or musculature in which edema is a factor.

U.S. Pat. No. 5,869,450, issued Feb. 9, 1999, to Wei et al., describes CRH analogs in which the fifth amino acid from the N-terminus is D-Pro or in the case of urocortin or sauvagine where the fourth amino acid from the N-terminus is D-Pro or D-Ser. These analogs have an anti-inflammatory activity and a disassociated ACTH response.

Cyclic CRH agonists have been described by Rivier et al. (U.S. Pat. Nos. 5,844,074 and 5,824,771). These CRH analogs, modified by cyclization of residues 30-33 of CRH via a glutamic acid-lysine bridge, are more potent than native CRH in the release of ACTH and. have lower molecular weights than native CRH. The elimination of residues 1-3 at the N-terminus of CRH has been shown to not alter biological activities or ACTH-release potency. (Kornreich et al., *J. Med. Chem.*, 35, pp. 1870-1876, 1992; Koerber et aL, *J. Med. Chem.*, 41(25), pp. 5002-5011, 1998.)

Tjuvajev et al. in *In Vivo*, 12, pp. 1-10, 1998 reported a series of in vivo and in vitro studies evaluating the antineoplastic potential of CRH in W256 rat mammary carcinoma. Using magnetic resonance imaging (MRI) and direct measurements of tumor and peritumoral brain water content they found that CRH treatment (100 micrograms/kg subcutaneously twice a day for 3 days) caused significant inhibition of growth of intracerebrally-injected W256 tumor cells. CRH also exhibited antiproliferative effects in in vitro cultures of W256 cells. The antiproliferative effects of CRH in W256 cells are believed to involve activation of nitric oxide synthase (NOS) and L-arginine-NO pathways.

In U.S. Pat. No. 6,319,900, Wei and Slominski disclose that CRH and members of the CRH superfamily, in which the $20^{th}$ amino acid is replaced with a D-amino acid, have anti-proliferative activity.

Human trials of CRH for the treatment of peritumoral brain edema have been initiated and preliminary data indicate that CRH reduces brain edema associated with tumor metastases. However, the limiting factor on the use of CRH has been the known blood-pressure lowering property of CRH. CRH causes relaxation of smooth muscles surrounding blood vessels (vasodilation) resulting in a lowering of blood-pressure. The resultant hypotension is sufficiently dangerous to limit the dosages of CRH that can be administered to humans. Overcoming this dose-limiting toxicity by design of CRH superfamily peptide analogs that have less blood-pressure lowering activity should improve the therapeutic index and provide useful anti-proliferative therapeutics.

SUMMARY OF THE INVENTION

This invention provides novel members of the corticiotropin-releasing hormone superfamily and peptide analogs thereof wherein the $38^{th}$ amino acid from the N-terminus is D-Nle, i.e. [D-Nle$^{38}$]-CRH peptide. In one embodiment, in addition to D-Ne$^{38}$, the $20^{th}$ amino acid from the N-terminus is a D-amino acid, i.e. [D-aa$^{20}$, D-Nle$^{38}$]-CRH peptide. In an alternative D-Nle$^{38}$ embodiment, amino acids 30 to 33 from the N-terminus are cyclized. i.e. cyclo(30-33)[D-Nle$^{38}$]CRH peptide. Particularly preferred are those CRH peptides of general formula cyclo(30-33)[D-Glu$^{20}$, D-Nle$^{38}$] CRH peptide. A representative member of this family is the peptide acetyl-cyclo(30-33)[D-Phe$^{12}$, D-Glu$^{20}$, Nle$^{21}$, Glu$^{30}$, D-His$^{32}$, Lys$^{33}$, D-Nle$^{38}$]-CRH(4-41).

Also provided are pharmaceutical compositions of the novel analogs formulated with pharmaceutically effective amounts of CRH peptide and pharmaceutically acceptable carriers. Such compositions may have from about 0.01% by weight to about 50% by weight of peptide, preferably from 0.1% to about 10%. The compositions may be formulated for oral, parenteral or topical delivery as appropriate for the indication under treatment. Topical delivery modalities include intrabuccal, intranasal, intraocular, transdermal, and rectal. The compositions may be provided in unit dosage form or formulated for sustained release of peptide. A preferred pharmaceutical composition contains a pharmaceutically effective amount of a peptide of the formula acetyl-cyclo(30-33)[D-Phe$^{12}$, D-Glu$^{20}$, Nle$^{21}$, Glu$^{30}$, D-His$^{32}$, Lys$^{33}$, D-Nle$^{38}$]-CRH(4-41) and a pharmaceutically acceptable carrier.

The peptides and their compositions are useful for treating proliferative disorders of the skin or other tissues, such as cancer and inflammatory dermatoses, particularly in human subjects. Cancers amenable to treatment with CRH peptides include, but are not limited to melanoma and squamous cell carcinoma; inflammatory dermatoses include, but are not limited to eczema and psoriasis. The peptide or peptides may be administered in an amount of from about 0.001 mg to about 1.0 mg/kg/day of patient body weight. In particular administration of an effective amount of a peptide of the formula acetyl-cyclo(30-33)[D-Phe$^{12}$, D-Glu$^{20}$, Nle$^{21}$, Glu$^{30}$, D-His$^{32}$, Lys$^{33}$, D-Nle$^{38}$]-CRH(4-41) is contemplated.

DEFINITIONS

The term "CRH peptide" as used herein refers to an analog of a member of the CRH family having one or more replacement amino acids.

The term "CRH superfamily" includes those peptides recognized in the art as belonging to the CRH family due to sequence similarities and similar biological activities. These include, but are not limited to, the peptides illustrated in Table 1. Thus, the CRH superfamily includes the CRH peptides originating with or derived from a number of species, e.g., rat, human, pig, sheep, cow, and fish, and also includes sauvagine, urotensin I and urocortin. A more comprehensive list of CRH superfamily peptides has recently been compiled (Trends in Pharmacological Sciences, 23:2, 71-77 (2002)), incorporated by reference herein.

TABLE 1

Peptides of the Corticotropin-Releasing Hormone Superfamily

| SEQ ID NO. | PEPTIDE | SPECIES | SEQUENCE[a][b] |
|---|---|---|---|
| 1 | CRH | Human/rat | SEEPPISLDL TFHLLREVLE MARAEQLAQQ AHSNRKLMEII |
| 2 | CRH | Pig | SEEPPISLDL TFHLLREVLE MARAEQLAQQ AHSNRKLMENF |
| 3 | CRH | Sucker fish | SEEPPISLDL TFHLLREVLE MARAEQLAQQ AHSNRKMMEIF |
| 4 | CRH | Sheep/Goat | SQEPPISLDL TFHLLREVLE MTKADQLAQQ AHSNRKLLDIA |
| 5 | CRH | Cow | SQEPPISLDL TFHLLREVLE MTKADQLAQQ AHNNRKLLDIA |
| 6 | Urotensin I | Sucker fish | NDDPPISIDL TFHLLRNMIE MARIENEREQ AGLNRKYLDEV |
| 7 | Urotensin I | Carp | NDDPPISIDL TFHLLRNMIE MARIENEREQ AGLNRKYLDEV |
| 8 | Urotensin I | Maggy sole | SEEPPMSIDL TFHMLRNMIH RAKMEGEREQ ALINRNLLDEV |
| 9 | Urotensin I | European flounder | SEDPPMSIDL TFHMLRNMIH MAKMEGEREQ AQINRNLLDEV |
| 10 | Urocortin | Rat | DDPPLSIDL TFHLLRTLLE LARTQSQRER AEQNRIIFDSV |
| 11 | Urocortin | Human | DNPSLSIDL TFHLLRTLLE LARTQSQRER AEQNRIIFDSV |
| 12 | Sauvagine | Frog | >EGPPISIDL SLELLRKMIE IEKQEKEKQQ AANNRLLLDTI |

[a]The carboxyl termini of these peptides are amidated.
[b]Single letter abbreviations for amino acids: S, T, P, A, G; Ser, Thr, Pro, Ala, Gly; M, L, I, V; Met; Leu, Ile, Val; E, D, N, Q; Glu, Asp, Asn, Gln; R, K, H; Arg, Lys, His; F, Y, W, Phe, Tyr, Trp; >E; proglutamyl

DETAILED DESCRIPTION OF THE INVENTION

This invention provides novel CRH peptides and their use for treating both benign and malignant cell proliferative disorders of the skin and other tissues. For example, the peptides of the instant invention can be used to treat diseases such as psoriasis, skin cancer and melanoma. Certain embodiments of the instant invention describe topical administration of corticotropin-releasing hormone (CRH) peptides to the affected area, while other embodiments describe parenteral delivery of the CRH peptides. The peptides themselves are synthetically derived, highly potent, and spatially constrained analogs of the naturally occurring hormone CRH and members of the CRH superfamily. U.S. Pat. No. 5,844,074, hereby incorporated by reference in its entirety, describes methods useful for the synthesis of these peptides.

The CRH peptides of this invention are based upon our discovery that replacing the thirty-eighth amino acid with a D-Nle provides improved anti-neoplastic and anti-cell proliferative activities without inducing significant hypotension. This substitution may be combined with the further substitution of a D-amino acid at position 20 in the case of the 41 amino acid containing peptides of the CRH superfamily or replacing the 19th residue of CRH superfamily peptides having 40 amino acid residues with a D-amino acid residue. In a preferred embodiment the D-amino acid is D-Glu. Also known in the art are CRH peptides having cyclic bonds, such as between the residues in the 30 and 33 position, which may be a disulfide linkage (between two Cys residues) but preferably is an amide-bond (i.e., a lactam bridge). Exemplary cyclic analogs are described in U.S. Pat. No. 5,844,074, issued Dec. 1, 1998, to Rivier, incorporated herein by reference. Such cyclic analogs may be suitable in practicing the subject invention, provided such cyclic analogs also have a D-Nle at position 38.

CRH and related CRH peptides have been found to inhibit Cloudman cell proliferation in vitro at picomolar levels. This effect is concentration-dependent and is inhibited by the non-selective CRH receptor antagonist, α-helical-CRH(9-41). The rank order of potency of CRH and CRH-related peptides provided insight into the CRH receptor subtype mediating the anti-proliferative effect. Replacement of residue 20 of CRH with a D-amino acid reduced the potency of CRH at the CRH2 receptor while activity at the CRH1 receptor was retained. The hypotensive activity of [D-Glu$^{20}$]-CRH relative to CRH is diminished, but suppressive effects on melanoma cell proliferation are retained. Two novel CRH peptides with D-amino acid substitutions are almost ten-fold more potent than CRH in suppressing cell proliferation possibly through activation of the CRH1 receptor. Similarly, CRH peptides were found to inhibit in vivo growth of B16 melanoma. Agonist activation of the CRH1 receptor signaling system in malignant melanocytes thus presents itself as a target for melanoma therapy. Further details may be found in Carlson, et al., *Anticancer Research* 21:1173-1180 (2001), incorporated herein by reference.

Since the peptides of this invention inhibit abnormal cell proliferation, they are useful in a number of different therapeutic applications. Specific tissues for which clinical usage of these peptides is contemplated include skin, as well as its adnexal structures such as hair follicle and sebaceous glands, and other epithelial tissues (eyelids, nasal membranes, oropharyngeal membranes, upper respiratory tract, esophagus, lower digestive tract), skeletal muscle, smooth muscle, cardiac muscle, blood vessels of the brain, blood vessels of the lungs and kidneys, and endometria. Where the tissues are not readily reached by topical administration (such as by creams and the like as further described hereinafter), then alternative modes of administration, such as oral or parenteral, may be used.

For example, therapeutic uses of these peptides include administration to treat disseminated cancers, including melanoma, squamous cell carcinoma, breast cancer, and uterine cancer, premalignant lesions such as lentigo maligna, actinic keratosis, and, for non-cancerous conditions, such as psoriasis, eczema, alopecia areata, hypertrichosis or keloids. The epithelial cells and keratinocytes are cells that line the base of the epidermis and form new cells which cover the surface of the body. These cells have a high metabolic activity and turnover; moreover, they participate in the inflammatory response, as they actively secrete cytokines and attract other inflammatory cells from the body (white blood cells). A disruption of keratinocyte activity is prominent in inflammatory dermatoses, of which psoriasis is a primary example. Other related conditions are eczema and various forms of dermatitis. Thus, an agent which inhibits keratinocyte proliferation may be useful for therapy of inflammatory dermatoses. For example, the basic lesion in psoriasis is hyperproliferation of keratinocytes in the epidermis. The turnover rate of these cells may be ten times more rapid than usual, and maturation of the cells is abnormal. (J. H. Stein, editor, Internal Medicine, chapter 216, "Psoriasis," pp. 1300-1302, 1998.)

The hair follicle-sebaceous gland unit of the skin, part of the "adnexa" or appendages of the skin is of pharmacological interest for these reasons:

(a) a large peptide such as a CRH peptide, with a molecular weight of four to five thousand daltons, can get to targets because it can be formulated to sit on the skin and penetrate along the hair shaft to the base of the hair follicle and to the sebaceous gland;

(b) proliferation of hair follicle cells can result in hypertrichosis, so a peptide like CRH may have value as a means for stopping excessive hair growth;

(c) proliferation of lymphocytes at the base of the hair follicle, a condition called lymphocytosis, poses a much serious problem, alopecia areata, in which there is excessive hair loss. This frequently occurs in women under stress and causes a strong emotional response, as the hair comes off in clumps and is cosmetically disfiguring. Current treatment, a steroid cream, is of limited effectiveness;

(d) proliferation of the epithelial cells of the sebaceous gland during puberty and other conditions of excessive dihydrotestosterone production contributes to the condition known as acne.

Typically a therapeutically effective dosage of a CRH peptide is at least about 0.01% w/w up to about 50% w/w or more, preferably more than 0.1% w/w of the active compound. The active ingredient may be administered at once, or may be divided into a number of smaller doses to be administered at intervals of time or as a controlled release formulation. The term "controlled release formulation" encompasses formulations that allow the continuous delivery of a CRH peptide to a subject over a period of time, preferably several days to weeks. Such formulations may administered subcutaneously or intramuscularly and allow for the continual steady release of a predetermined amount of drug in the subject over time. The controlled-release formulation of CRH peptide may be, for example, a formulation of drug-containing polymeric microcapsules, such as those described in U.S. Pat. Nos. 4,677,191 and 4,728,721, incorporated herein by reference. Alternatively, the controlled-release formulation of CRH peptide may employ an osmotic pump, e.g. the Alzet pump, commercially available from Alza, Palo Alto, Calif. The dosage of CRH peptide released by the sustained-release formulation is preferably about 5-300 microgram/kg/day, and more preferably 10-50 microgram/kg/day. In another embodiment the controlled release formulation may be provided in a transdermal (or other tissue) delivery device, employing, for example concentration gradients or iontophoresis to drive delivery of the CRH peptide.

The precise dosage and duration of treatment will be a function of the condition being treated and may be determined empirically using known testing protocols or by extrapolation from in vivo or in vitro test data. Concentrations and dosage values may also vary with the age of the individual treated. For any particular subject, specific dosage regimens should be adjusted over time according to the individual need and the professional judgment of the person administering or supervising the administration of the formulations and that the concentration ranges set forth herein are exemplary only and are not intended to limit the scope or practice of the claimed invention.

The CRH peptides may be suspended in micronized or other suitable form and may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the proliferative condition and may be empirically determined.

Preferable concentrations are in the range of 0.01% w/w to about 25% w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

Suitable therapeutic formulations include solutions, suspensions, emulsions and the like and may be formulated as creams, gels, ointments, emulsions, solutions, elixirs, lotions, suspensions, tinctures, pastes, foams, aerosols, irrigations, sprays, suppositories, bandages, or in any other form suitable for delivery of the CRH peptide to the target tissue, including oral, parenteral, and topical formutions. Processes for producing acceptable formulations are known to the skilled artisan and are disclosed, inter alia, in Remington: The Science and Practice of Pharmacy, Mack Publishing Co, 1995, incorporated by reference herein.

Pharmaceutical and cosmetic carriers or vehicles suitable for administration of the CRH peptides provided herein include any such carriers known to those skilled in the art to be suitable for the particular mode of administration. In addition, the CRH peptides may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

For topical administration, the CRH peptides may be formulated as gels, creams, lotions, solids, solutions or suspensions, or aerosols. Compositions for treating human skin are formulated for topical application with an anti-proliferative effective amount of one or more of the peptides selected as described herein, in an effective concentration range (by weight), between about 0.1% and 80%, preferably 0.1 to 50%, more preferably greater than about 1% up to about 50% or more in a cream, ointment, lotion, gel, solution or solid base or vehicle known in the art to be nontoxic and dermatologically acceptable or suitable for application to the mucosa. Aqueous suspensions are preferably formulated at concentrations greater than about 1% w/w, more preferably 2% w/w.

To formulate a composition, the weight fraction of CRH peptide is dissolved, suspended, dispersed or otherwise mixed in a selected vehicle at an effective concentration such that the proliferative condition is relieved or ameliorated. Generally, emollient or lubricating vehicles that help hydrate the skin are preferred to volatile vehicles, such as ethanol that dry the skin. Examples of suitable bases or vehicles for preparing compositions for use with human skin are petrolatum, petrolatum plus volatile silicones, lanolin, cold cream, and hydrophilic ointment.

The choice of an acceptable vehicle is largely determined by the mode of application and tissue to be treated. Suitable pharmaceutically and dermatologically acceptable vehicles for topical application include lotions, creams, solutions, gels, tapes and the like. Generally, the vehicle is either organic in nature or an aqueous emulsion and capable of having the selected peptide, which may be micronized, dispersed, suspended or dissolved therein. The vehicle may include pharmaceutically-acceptable emollients, skin penetration enhancers, coloring agents, fragrances, emulsifiers, thickening agents, and solvents.

Suitable lotions contain an effective concentration of one or more of the peptides. The effective concentration is preferably effective to deliver an anti-proliferative amount, typically at a concentration of between about 0.1-50% w/w or more of one or more of the CRH peptides provided herein. The lotions may also contain from 1% to 50% w/w, preferably from 3% to 15% w/w of an emollient and the balance water, a suitable buffer, a $C_2$ or $C_3$ alcohol, or a mixture of water of the buffer and the alcohol. Any emollients known to those of skill in the art as suitable for application to human skin may be used.

Suitable creams are formulated to contain concentration effective to deliver an anti-proliferative effective amount of the CRH peptide to the treated tissue, typically from about 0.1%, preferably from about 1% to about 50%, preferably between about 5% and 15% of one or more of the CRH peptides provided herein. The creams may also contain from 5% to 50%, preferably from 10% to 25%, of an emollient and the remainder is water or other suitable non-toxic carrier, such as an isotonic buffer. The cream may also contain a suitable emulsifier, at a level from 3% to 50%, preferably from 5% to 20%.

Solutions and suspensions for topical administration are formulated to contain an amount of one or more CRH peptides effective to deliver an anti-proliferative amount, typically at a concentration of between about 0.01 and about 50% w/w, preferably at least 1% w/w, of one or more of the peptides. The balance may be water, a suitable organic solvent or other suitable solvent or buffer. Suitable organic solvents include propylene glycol, polyethylene glycol (M. W. 200-600), polypropylene glycol (M. W. 425-2025), glycerine, sorbitol esters, 1,2,6-hexanetriol ethanol, isopropanol, diethyltartrate, butanediol and mixtures thereof. Such solvent systems may also contain water.

Solutions or suspensions useful for local application may include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Liquid preparations may be enclosed in ampoules, disposable syringes or multiple dose vials made of glass, plastic or other suitable material. Suitable carriers may include physiological saline or phosphate buffered saline (PBS), and the suspensions and solutions may contain thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

Suitably prepared solutions and suspension may also be topically applied to the eyes and mucosa. Solutions, particularly those intended for ophthalmic use, may be formulated as 0.01%-10% w/w isotonic solutions, pH about 5-7, with appropriate salts, and preferably containing one or more of the CRH peptides at a concentration of about 0.1% w/w to 50% w/w or more. Suitable ophthalmic solutions are known (see, e.g. U.S. Pat. No. 5,116,868, incorporated herein, which describes ophthalmic irrigation solutions).

Gel compositions can be formulated by simply admixing a suitable thickening agent to the previously described solution or suspension composition. Examples of suitable thickening agents have been previously described with respect to the lotions. The gelled compositions contain an effective amount of one or more of a CRH peptide, typically at a concentration of between about 0.1 and about 50% w/w, preferably from 1 0% to 50% w/w, of an organic solvent; from 0.5% to 20% w/w, preferably from 1% to 10% w/w of the thickening agent; the balance being water or other aqueous carrier.

EXAMPLES

The following Examples are offered to illustrate, but not to limit the claimed invention.

Example 1

CRH Peptide Synthesis

CRH and CRH peptides used in these Examples have or are based upon the human-rat CRH sequence. For urocortin, the human sequence was used. CRH, urocortin, sauvagine, and α-helical-(9-41)-CRH were obtained from Phoenix Pharmaceuticals, Belmont, Calif. [D-Pro$^5$]-CRH, [D-Glu$^{20}$]-CRH, acetyl-cyclo(30-33)[D-Phe$^{12}$, D-Glu$^{20}$, Nle$^{21}$, Glu$^{30}$, D-His$^{32}$, $^{Lys33}$, D-Nle$^{38}$]-CRH(4-41), and acetyl-cyclo(30-33)[D-Phe$^{12}$, Nle$^{18}$, D-Glu$^{20}$, Nle$^{21}$, Glu$^{30}$, D-Ala$^{32}$]-urotensin I(4-41) were custom synthesized by Dr. Janos Varga (California Peptide Research, Inc., Napa, Calif.) using standard solid-phase techniques. The purities of the synthesized peptides, as determined by HPLC in two buffer systems, were 95 to 99% and the principal peak of the mass spectrum for each peptide corresponded with the calculated average mass. For all peptides the amino acid analysis gave the expected ratio of amino acids. The peptides were stored in vacuo at room temperature. Peptides were weighed and dissolved in sterile water containing 0.5% bovine serum albumin (BSA) to a concentration of 10 mM and frozen at −70° C. 10 mM stock solutions of peptides were diluted on experimental days with incubation medium for subsequent in vitro studies.

Example 2

In vitro Assay

S91 mouse Cloudman cells (cell line M3) were obtained from the American Type Culture Collection. Hams F-10 medium, fetal bovine serum, and horse serum were obtained from Gibco BRL. Cloudman cells were cultured in Ham's F-10 medium supplemented with 5% horse serum, 2.5% fetal bovine serum, and 1% penicillin/streptomycin in a humidified incubator with 5% C02 at 37° C. Media were changed every second day.

Cells were plated at a concentration of ~20,000 cells per well in Ham's F-10 medium supplemented with 5% horse serum, 2.5% fetal bovine serum and 1% penicillin/streptomycin into tissue-culture-12-well plates. Test peptides or sterile water containing 0.5% BSA (vehicle control) were added to culture medium prior to plating, and cells were allowed to adhere overnight in a humidified incubator with 5% $CO_2$ at 37° C. Culture medium containing peptides and culture medium containing vehicle control were changed daily. For counting, cells were detached with 200 μL of 0.25% trypsin. Detachment levels were verified under a light microscope. After detachment, cell suspensions were transferred to 1.5-mL Eppendorf tubes, vigorously pipetted for uniform suspension, and cell number in 10 μL of cell suspension was counted in a hemacytometer under a light microscope.

CRH and CRH peptides were found to inhibit growth of Cloudman melanoma cells in vitro in a concentration-dependent manner. Significant anti-proliferative effects were observed with CRH at the higher concentrations by the end of the first 24-hr measurement period, and maximum suppression occurred about 96 hr after treatment. The EC50 of CRH after 96 hr was 9 (SE 3) pM. No enhancement of the anti-proliferative effects was observed after 96 hr of CRH treatment, at least out to the end of the study period, which was 14 days. Other members of the CRH peptide family—sauvagine (frog), urotensin I (fish), and urocortin (human)—were also evaluated, as were three synthetic analogs of CRH, for anti-proliferative effects on Cloudman cells. Like CRH, the three CRH-related peptides sauvagine, urocortin, and the urotensin analog acetyl-cyclo(30-33)[D-Phe$^{12}$, Nle$^{18}$,D-Glu$^{20}$, Nle$^{21}$, D-Ala$^{32}$]-urotensin I(4-41) were highly effective in suppressing proliferation of Cloudman cells (Table 2). Two new potent CRH analogs [D-Glu$^{20}$]-CRH and acetyl-cyclo(30-33)[D-Phe$^{12}$, D-Glu$^{20}$, Nle$^{21}$, Glu$^{30}$, D-His$^{32}$, Lys$^{33}$, D-Nle$^{38}$]-CRH(4-41)(Peptide IV of Table 2), were found to significantly inhibit proliferation. The synthetic analog acetyl-cyclo (30-33)[D-Phe$^{12}$, Nle$^{18}$, D-Glu$^{20}$, Nle$^{21}$, Glu$^{30}$, D-Ala$^{32}$]-urotensin 1(4-41) (Peptide V of Table 2) was the most potent, with an EC50 10-fold lower than that of CRH. [D-Pro$^5$]-CRH, a CRH2 receptor-selective agonist was less active than CRH with an EC50 10-fold greater than CRH. The rank order potencies of the natural peptides of the CRH family—CRH~urocortine~sauvagine—suggests that the anti-proliferative effects were mediated by CRH1 receptors.

TABLE 2

$EC_{50}$ values for CRH peptides versus Cloudman melanoma

| Peptide | $EC_{50}$(+/−Std. Error) picomolar |
|---|---|
| I. CRH | 8.6 (2.9) |
| II. [D-Glu$^{20}$]-CRH | 16 (4.6) |
| III. [D-Pro$^5$]-CRH | 82 (14) |
| IV. Ac-[D-Nle$^{38}$]-CRH(4-41) | 0.48 (0.2) |
| V. Ac-[D-Ala$^{32}$]-urotensin I | 0.36 (0.1) |
| VI. Urocortin | 9.5 (4.1) |
| VII. Sauvagine | 7.8 (1.9) |

Example 3

In Vivo Assay

Female C57B1/6 mice, weighing 20-25 g, were inoculated subcutaneously (s.c.) with B16 melanoma cells. Mice were randomized into different groups and injected 3 to 7 days after inoculation with saline (control) or acetyl-cyclo (30-33)[D-Phe$^{12}$, D-Glu$^{20}$, Nle$^{21}$, Glu$^{30}$, D-His$^{32}$, Lys$^{33}$, D-Nle$^{38}$]-CRH(4-41) s.c. each day for 5 days at 0.1 or 0.2 mg/kg acetyl-cyclo(30-33)[D-Phe$^{12}$, D-Glu$^{20}$, Nle$^{21}$, Glu$^{30}$, D-His$^{32}$, Lys$^{33}$, D-Nle$^{38}$]-CRH(4-41). The tumor volume was estimated using a caliper-ruler; tumor size (mm$^3$) was calculated by multiplying the long axis by the square of the short axis divided by 2. Inhibition of tumor volume was observed 12 and 14 days after inoculation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method for treating melanoma in a human subject which method comprises administering to the subject an effective amount of a peptide analog of a Corticotropin-Releasing Hormone (CRH) having the amino acid sequence of human CRH (SEQ ID NO:1), wherein the 38th amino acid from the N-terminus is D-Nle.

2. A method of claim 1 wherein the peptide analog is administered in an amount of from about 0.001 mg/kg/day to about 1.0 mg/kg/day of patient body weight.

3. A method for treating melanoma in a human subject which method comprises administering an effective amount of a peptide analog of the formula acetyl-cyclo(30-33)[D-Phe$^{12}$, D-Glu$^{20}$, Nle$^{21}$, Glu$^{30}$, D-His$^{32}$, Lys$^{33}$, D-Nle$^{38}$]-CRH(4-41) to the subject.

* * * * *

SEQUENCE LISTING

```
<160> NUMBER OF SEQ ID NOS: 12

<210> SEQ ID NO 1
<211> LENGTH: 41
<212> TYPE: PRT
<213> ORGANISM: Homo sapiens
<220> FEATURE:
<223> OTHER INFORMATION: CRH peptide

<400> SEQUENCE: 1

Ser Glu Glu Pro Pro Ile Ser Leu Asp Leu Thr Phe His Leu Leu Arg
  1               5                  10                  15

Glu Val Leu Glu Met Ala Arg Ala Glu Gln Leu Ala Gln Gln Ala His
             20                  25                  30

Ser Asn Arg Lys Leu Met Glu Ile Ile
         35                  40

<210> SEQ ID NO 2
<211> LENGTH: 41
<212> TYPE: PRT
<213> ORGANISM: Sus sp.
<220> FEATURE:
<223> OTHER INFORMATION: CRH peptide

<400> SEQUENCE: 2

Ser Glu Glu Pro Pro Ile Ser Leu Asp Leu Thr Phe His Leu Leu Arg
  1               5                  10                  15

Glu Val Leu Glu Met Ala Arg Ala Glu Gln Leu Ala Gln Gln Ala His
             20                  25                  30

Ser Asn Arg Lys Leu Met Glu Asn Phe
         35                  40

<210> SEQ ID NO 3
<211> LENGTH: 41
<212> TYPE: PRT
<213> ORGANISM: Pterygoplichthys sp.
<220> FEATURE:
<223> OTHER INFORMATION: CRH peptide

<400> SEQUENCE: 3

Ser Glu Glu Pro Pro Ile Ser Leu Asp Leu Thr Phe His Leu Leu Arg
  1               5                  10                  15

Glu Val Leu Glu Met Ala Arg Ala Glu Gln Leu Ala Gln Gln Ala His
             20                  25                  30

Ser Asn Arg Lys Met Met Glu Ile Phe
         35                  40

<210> SEQ ID NO 4
<211> LENGTH: 41
<212> TYPE: PRT
<213> ORGANISM: Oreamnos americanus
<220> FEATURE:
<223> OTHER INFORMATION: CRH peptide

<400> SEQUENCE: 4

Ser Gln Glu Pro Pro Ile Ser Leu Asp Leu Thr Phe His Leu Leu Arg
```

```
                1               5                  10                 15
Glu Val Leu Glu Met Thr Lys Ala Asp Gln Leu Ala Gln Gln Ala His
                        20                  25                  30

Ser Asn Arg Lys Leu Leu Asp Ile Ala
            35                  40

<210> SEQ ID NO 5
<211> LENGTH: 41
<212> TYPE: PRT
<213> ORGANISM: Bos taurus
<220> FEATURE:
<223> OTHER INFORMATION: CRH peptide

<400> SEQUENCE: 5

Ser Gln Glu Pro Pro Ile Ser Leu Asp Leu Thr Phe His Leu Leu Arg
 1               5                  10                  15

Glu Val Leu Glu Met Thr Lys Ala Asp Gln Leu Ala Gln Gln Ala His
                        20                  25                  30

Asn Asn Arg Lys Leu Leu Asp Ile Ala
            35                  40

<210> SEQ ID NO 6
<211> LENGTH: 41
<212> TYPE: PRT
<213> ORGANISM: Pterygoplichthys sp.
<220> FEATURE:
<223> OTHER INFORMATION: Urotensin I peptide

<400> SEQUENCE: 6

Asn Asp Asp Pro Pro Ile Ser Ile Asp Leu Thr Phe His Leu Leu Arg
 1               5                  10                  15

Asn Met Ile Glu Met Ala Arg Ile Glu Asn Glu Arg Glu Gln Ala Gly
                        20                  25                  30

Leu Asn Arg Lys Tyr Leu Asp Glu Val
            35                  40

<210> SEQ ID NO 7
<211> LENGTH: 41
<212> TYPE: PRT
<213> ORGANISM: Carassius sp.
<220> FEATURE:
<223> OTHER INFORMATION: Urotensin I peptide

<400> SEQUENCE: 7

Asn Asp Asp Pro Pro Ile Ser Ile Asp Leu Thr Phe His Leu Leu Arg
 1               5                  10                  15

Asn Met Ile Glu Met Ala Arg Ile Glu Asn Glu Arg Glu Gln Ala Gly
                        20                  25                  30

Leu Asn Arg Lys Tyr Leu Asp Glu Val
            35                  40

<210> SEQ ID NO 8
<211> LENGTH: 41
<212> TYPE: PRT
<213> ORGANISM: Hippoglossoides sp.
<220> FEATURE:
<223> OTHER INFORMATION: Urotensin I peptide

<400> SEQUENCE: 8

Ser Glu Glu Pro Pro Met Ser Ile Asp Leu Thr Phe His Met Leu Arg
 1               5                  10                  15

Asn Met Ile His Arg Ala Lys Met Glu Gly Glu Arg Glu Gln Ala Leu
```

```
                     20                  25                  30

Ile Asn Arg Asn Leu Leu Asp Glu Val
            35                  40

<210> SEQ ID NO 9
<211> LENGTH: 41
<212> TYPE: PRT
<213> ORGANISM: Platichthys flesus
<220> FEATURE:
<223> OTHER INFORMATION: Urotensin I peptide

<400> SEQUENCE: 9

Ser Glu Asp Pro Pro Met Ser Ile Asp Leu Thr Phe His Met Leu Arg
 1               5                  10                  15

Asn Met Ile His Met Ala Lys Met Glu Gly Glu Arg Glu Gln Ala Gln
                20                  25                  30

Ile Asn Arg Asn Leu Leu Asp Glu Val
            35                  40

<210> SEQ ID NO 10
<211> LENGTH: 40
<212> TYPE: PRT
<213> ORGANISM: Rattus sp.
<220> FEATURE:
<223> OTHER INFORMATION: Urocortin peptide

<400> SEQUENCE: 10

Asp Asp Pro Pro Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
                20                  25                  30

Asn Arg Ile Ile Phe Asp Ser Val
            35                  40

<210> SEQ ID NO 11
<211> LENGTH: 40
<212> TYPE: PRT
<213> ORGANISM: Homo sapiens
<220> FEATURE:
<223> OTHER INFORMATION: Urocortin peptide

<400> SEQUENCE: 11

Asp Asn Pro Ser Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
                20                  25                  30

Asn Arg Ile Ile Phe Asp Ser Val
            35                  40

<210> SEQ ID NO 12
<211> LENGTH: 40
<212> TYPE: PRT
<213> ORGANISM: Xenopus sp.
<220> FEATURE:
<223> OTHER INFORMATION: Sauvagine peptide

<400> SEQUENCE: 12

Glu Gly Pro Pro Ile Ser Ile Asp Leu Ser Leu Glu Leu Leu Arg Lys
 1               5                  10                  15
```

```
Met Ile Glu Ile Glu Lys Gln Glu Lys Glu Lys Gln Gln Ala Ala Asn
            20                  25                  30

Asn Arg Leu Leu Leu Asp Thr Ile
        35                  40
```